(12) United States Patent  
McKendry et al.

(10) Patent No.: US 6,706,012 B2
(45) Date of Patent: Mar. 16, 2004

(54) APPARATUS FOR EXPRESSING MILK

(75) Inventors: Bruce McKendry, Benicia, CA (US); Wallace Charles Seaman, Cool, CA (US); Sung Lee, Elk Grove, CA (US)

(73) Assignee: L. Jason Clute, Alamo, CA (US)

( * ) Notice: Subject to any disclaimer, the term of this patent is extended or adjusted under 35 U.S.C. 154(b) by 0 days.

(21) Appl. No.: 09/876,891

(22) Filed: Jun. 7, 2001

(65) Prior Publication Data

US 2003/0004459 A1 Jan. 2, 2003

Related U.S. Application Data

(63) Continuation-in-part of application No. 09/715,990, filed on Nov. 17, 2000, which is a continuation-in-part of application No. 09/591,981, filed on Jun. 12, 2000.

(51) Int. Cl.[7] .................................................. A61M 1/06
(52) U.S. Cl. ............................ 604/74; 604/75; 604/76; 119/14.02
(58) Field of Search .................... 119/14.02; 604/74–76, 604/320, 315, 346, 14; 422/101; 251/208; 417/415

(56) References Cited

U.S. PATENT DOCUMENTS

| 4,263,912 A | 4/1981 | Adams ........................ 128/281 |
| 4,607,596 A | * 8/1986 | Whittlestone et al. ... 119/14.02 |
| 4,772,262 A | * 9/1988 | Grant et al. ................... 604/74 |
| 4,892,517 A | 1/1990 | Yuan et al. ..................... 604/74 |
| 5,071,403 A | * 12/1991 | Larsson ....................... 604/320 |
| 5,358,476 A | 10/1994 | Wilson .......................... 604/74 |
| 5,542,921 A | 8/1996 | Meyers et al. ................. 604/74 |
| 5,749,850 A | 5/1998 | Williams et al. .............. 604/74 |
| 5,776,098 A | 7/1998 | Silver et al. ................... 604/74 |
| 6,287,521 B1 | 9/2001 | Quay et al. ................. 422/101 |
| 6,290,671 B1 | * 9/2001 | Niederberger .............. 604/119 |

* cited by examiner

Primary Examiner—Brian L. Casler
Assistant Examiner—Roz Ghafoorian
(74) Attorney, Agent, or Firm—Greer, Burns & Crain, Ltd.

(57) ABSTRACT

A device for expressing milk from one or more breasts has at least one, and preferably two expressers and a pump. The expressers each have a cup for fitting on the breasts and a cup outlet to which a vacuum created by the pump can be connected. The cups have a flexible liner which collapses around the breast to establish the vacuum. Pulsating pressure is applied to the outside of the liner to increase the vacuum and stimulate milk production. The pressure is applied through lines which are vented to maintain adequate, consistent pressure pulses without stalling the pump.

9 Claims, 5 Drawing Sheets

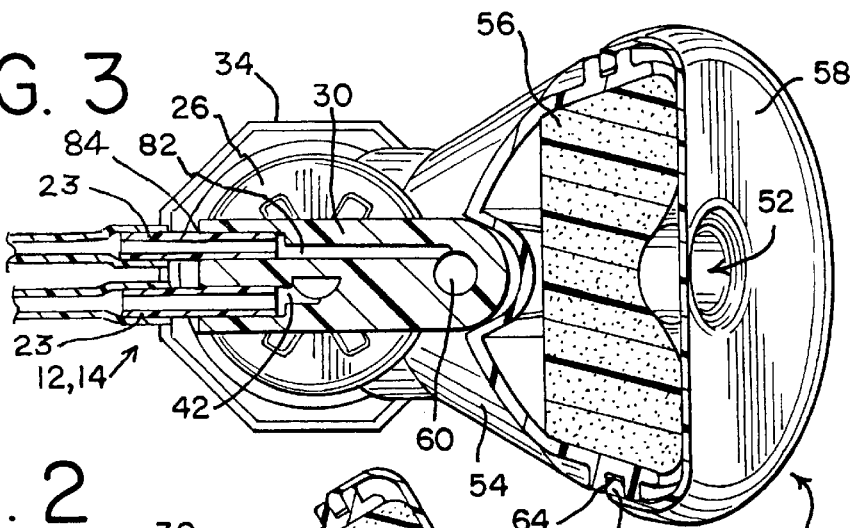
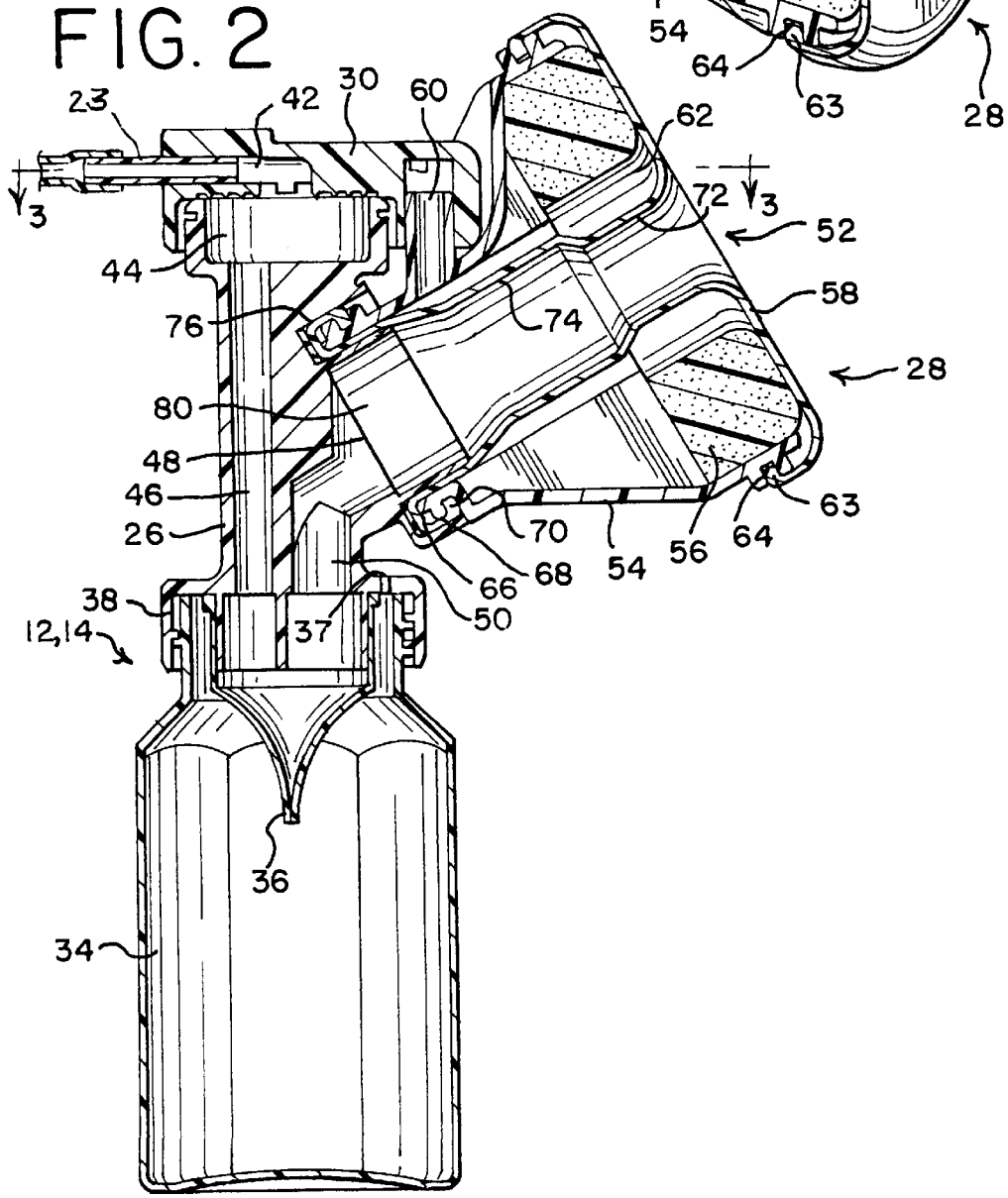

APPARATUS FOR EXPRESSING MILK

This is a continuation-in-part of Ser. No. 09/715,990, filed Nov. 17, 2000, which is a continuation-in-part of Ser. No. 09/591,981, filed Jun. 12, 2000.

FIELD OF THE INVENTION

This invention relates to apparatus for extracting milk, and more particularly, to breast pumps which are convenient and comfortable to use.

BACKGROUND OF THE INVENTION

Pumps for expressing milk from breasts are well-known. One known breast pump is disclosed in Whittlestone U.S. Pat. No. 4,607,596.

The Whittlestone patent discloses a breast pump having two milk collectors connected to a pump which applies both a vacuum and pulsating pressure to the breasts to extract milk. The pulsating pressure reciprocates between positive and negative (vacuum) pressure. The pulsating pressure gently massages and compresses the breasts to stimulate milk production, and the vacuum secures the milk collectors to the breasts and helps draw the milk and collect it. The pulsating pressure actually cyclically increases the vacuum level at the breast(s), which further stimulates milk production. However, the pressure is not relieved during pulsation in the Whittlestone patent, so pressure can build to a level sufficient to stall a small motor in a well-sealed system. In addition, the amplitude of the pressure pulses can be reduced by pressure build-up, which is also undesirable. Thus, there is a need for breast pumps that use pulsation as well as vacuum to draw milk, and have controlled relief of the pressure during operation.

In the Whittlestone device, milk from the two collectors is commonly drawn into a first collection vessel, and then a second collection vessel. The milk is drawn through vacuum lines, though, which makes cleaning difficult. Accordingly, there is a need for breast pumps which are more sanitary and easier to clean than the Whittlestone device.

The Whittlestone patent discloses a breast cup having a housing, a relatively soft inner ring or donut, and a flexible liner. The liner wraps around the outlet of the cup, and a bung is inserted into the cup outlet to pass the vacuum and milk. At the inlet side, the liner is simply folded over the outside of the housing. This design has limitations. The liner is not accurately aligned and reliably sealed on the inlet side, so moisture and other contaminants can get inside the liner, which is undesirable. At the outlet, the nipple can contact the bung and the liner can collapse around the breast, which can be uncomfortable, and can cause unnecessary trauma, including potential abrasion at the tip of the nipple. Accordingly, there is a need for breast pumps having cups which better fix the liner to the housing. There is also a need for breast pump cups which protect at least the end of the nipple from discomfort due to pulsating pressure.

The breast pump disclosed in the Whittlestone patent is a diaphragm pump operated by an electric motor. Rotation of the motor shaft is translated into back and forth action by a somewhat large and cumbersome linkage which moves the diaphragm. This adds not only size but weight to the pump, as well. Moreover, the motor must be fairly large, in part because a high vacuum is needed for cleaning purposes, and to maintain adequate vacuum and pressure if the system is leaky. These are problems because convenient storage and portability are desirable to breast pump users. Thus, there is a need for breast pumps which are lighter and smaller than known devices.

Accordingly, one object of this invention is to provide new and improved apparatus for extracting milk from breasts.

Another object is to provide new and improved breast pumps which are more convenient and comfortable to use.

Another object is to provide new and improved breast pumps that use both vacuum and pulsation pressure to collect milk, and control the pulsation pressure to maintain consistent, predetermined increases in the vacuum as the milk is collected.

Still a further object is to provide new and improved breast pumps which are more sanitary, easy to clean and easy to disassemble and re-assemble in the field.

Yet another object is to provide new and improved breast pumps which are relatively light, compact and portable.

SUMMARY OF THE INVENTION

A device for expressing milk from one or both breasts has at least one milk collector and a pump. Preferably, the device has first and second collectors (also called expressers), so that both breasts can be milked simultaneously. Each expresser has a cup assembly which fits on the breast, a pulsation port to which a supply of pressurized pulsating air is connected, and a vacuum port to which a vacuum supply is connected. The pulsating air and vacuum are created by the pump. In use, pulsating air causes massage and gentle compression of the breast and stimulates milk production, while the vacuum secures a liner in the collector on the breast and expresses the milk from the breast. Among other things, the pressure pulses increase the vacuum at the breast.

Both vacuum and pulsating air pressure are fairly well controlled by adequately sealing the various parts of the device and providing a pressure release vent for the pressurized air supply to each expresser. A vacuum adjustment is also provided.

The collectors also include a cap and manifold which direct the vacuum and pressure, a cup assembly which is preferably press fit onto the manifold, a collection vessel secured to the bottom of the manifold, and, if desired, a one-way check valve or the like between the manifold and the collection vessel. After passing through the vacuum adjustment, the vacuum is directed through the cap and manifold, collection vessel and cup assembly so that the milk is drawn into the collector with little or no milk entering the vacuum lines to the pump. A filter may be provided for added isolation of the vacuum pump and vacuum lines, if desired.

The cup assembly includes a bell housing, a relatively soft donut shaped pad, and the flexible liner, preferably made of silicone, nitrile or other suitable material that meets requirements for medical materials. The liner is secured to the inlet side of the cup assembly by a locking type of attachment, and extends around the bottom or lower end of the bell housing, where it is secured by another locking press fit configuration.

The bottom end of the cup assembly fits into a receptacle in the manifold. The receptacle has a hollow boss which extends into the cup assembly by a desired distance. The hollow portion inside the boss increases the area for extension of the nipple during milk expression, avoiding potentially uncomfortable contact at the nipple area. The boss also prevents the liner from collapsing around the end of the nipple during use, and keeps the throat of the cup assembly open for milk flow.

The collector can be easily disassembled and cleaned in a dishwasher or the like, by removing the collection vessel and using or storing the milk, removing the cap and then removing the cup assembly. The cup assembly can be cleaned without removing the liner, if desired, or the liner can be removed and cleaned separately, or replaced. A cleaning cap can be placed over the air pulsation port of the cup assembly when the cup assembly is cleaned in its assembled condition, to prevent water from entering the space between the liner and the bell housing. A valve could be used in place of the cap for this purpose, if desired.

The manifold, cap and valve can also be washed. The cup assembly can be easily reassembled after cleaning by reinserting the cup assembly in the manifold, re-attaching the cap to the manifold and cup assembly, and securing another collection vessel to the bottom of the manifold, with or without the check valve.

The pump includes a movable diaphragm in a chamber. The diaphragm is oscillated back and forth by a relatively small linear actuator device such as a stepper motor. The motor preferably is a self-contained system that moves its final object axially. The motor can have a shaft which does not rotate, but moves back and forth axially. The shaft of the motor is directly or nearly directly linked to the diaphragm, which eliminates complex and cumbersome linkage components, reducing the size and weight of the pump.

BRIEF DESCRIPTION OF THE DRAWINGS

The above mentioned and other features of this invention and the manner of obtaining them will become more apparent, and the invention itself will be best understood with reference to the following description of an embodiment of the invention taken in conjunction with the accompanying drawings, in which:

FIG. 2 is a milk collector used in the apparatus of FIG. 1, shown in cross-section;

FIG. 3 is a top view of the milk collector of FIG. 2, taken along lines 3—3 in FIG. 2;

DETAILED DESCRIPTION

Figure 1:
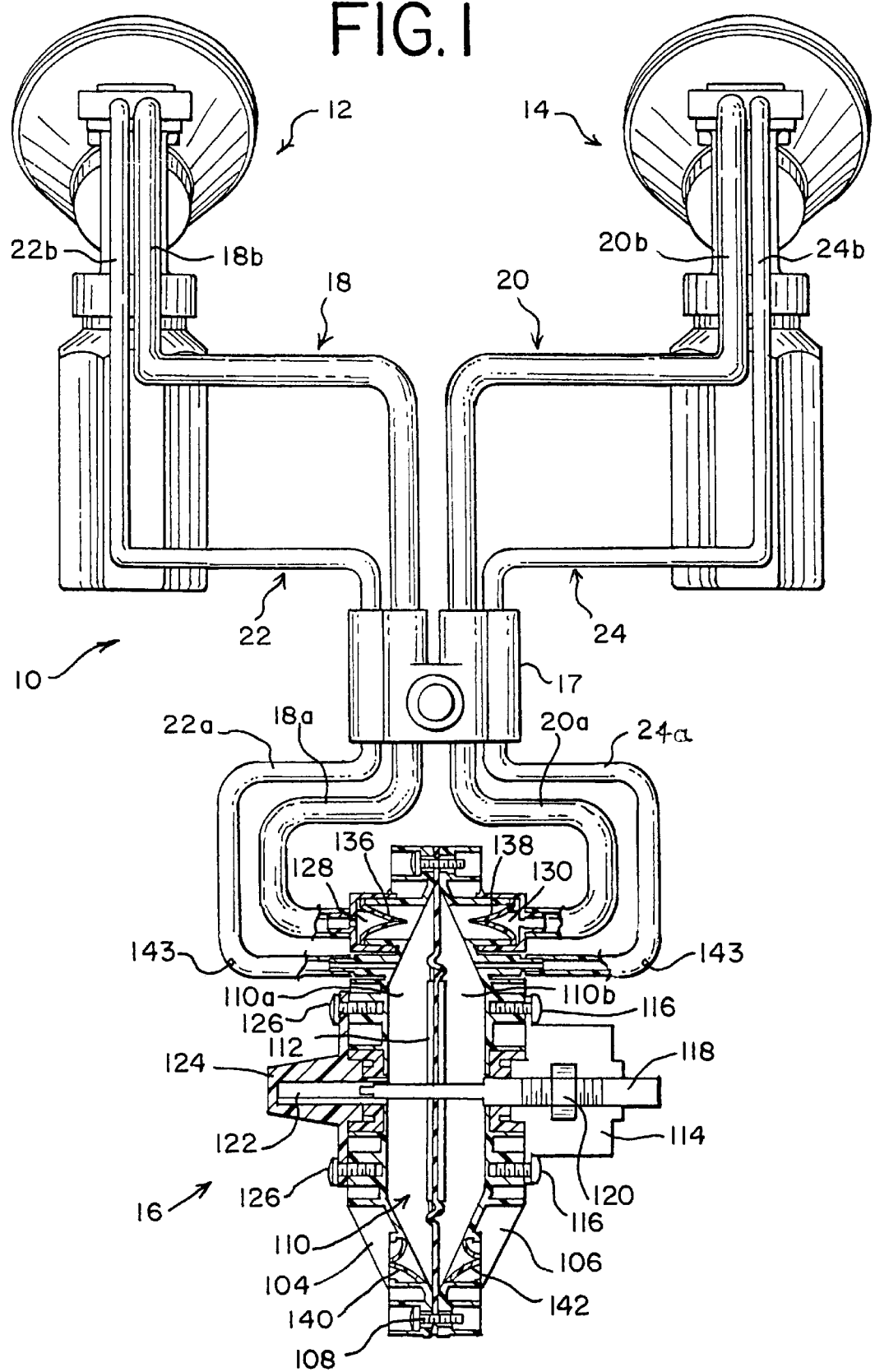
FIG. 1 is a partially cut-away perspective view of apparatus made in accordance with the principles of this invention.

Referring to FIG. 1, apparatus 10 is provided for expressing milk from one breast, or from two breasts simultaneously. The apparatus 10 includes a first collector or expresser 12 and a second expresser 14. It is likely that both expressers would generally be used, but only one expresser could be used, if desired, preferably by disconnecting the vacuum line from the unused expresser and covering the unused vacuum port of the pump with a cap (not shown).

Figure 12:
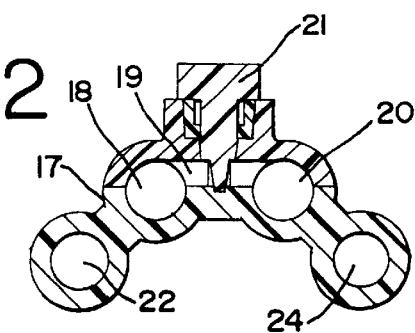
FIG. 12 is a cutaway view of a connector used in the apparatus of FIG. 1.

A pump 16 is connected to both expressers 12, 14 through vacuum lines 18, 20, and air pressure lines 22, 24. The vacuum and pulsation lines can be configured in any suitable way. In FIG. 1, vacuum hoses 18a, 20a and pressure hoses 22a, 24a are connected to the pump 16 and a connector 17. Vacuum hoses 18b, 20b and pressure hoses 22b, 24b are connected to the other end of the connector 17 and the expressers 12, 14 with adapters 23 (FIGS. 2, 3), if needed. The connector 17 has openings for the lines 18, 20, 22 and 24, and a throat 19 which connects the vacuum lines 18, 20 to each other, creating a common vacuum at the expressers 12, 14, as seen in FIG. 12. A threaded needle valve 21 in the throat 19 permits easy adjustment of the vacuum by venting atmospheric air into the system as desired. The connector 17 can be secured to a housing, if desired, to provide easy vacuum and pressure transmission through the housing.

The pump 16 creates a vacuum which engages the breasts, and contributes to drawing the milk from the breasts. The pump also creates reciprocating compression and release pressure pulsation around the areola and some or all of the nipple, as will be seen. The pump 16 can be powered by line voltage, a battery, manually or the like.

Figure 5:
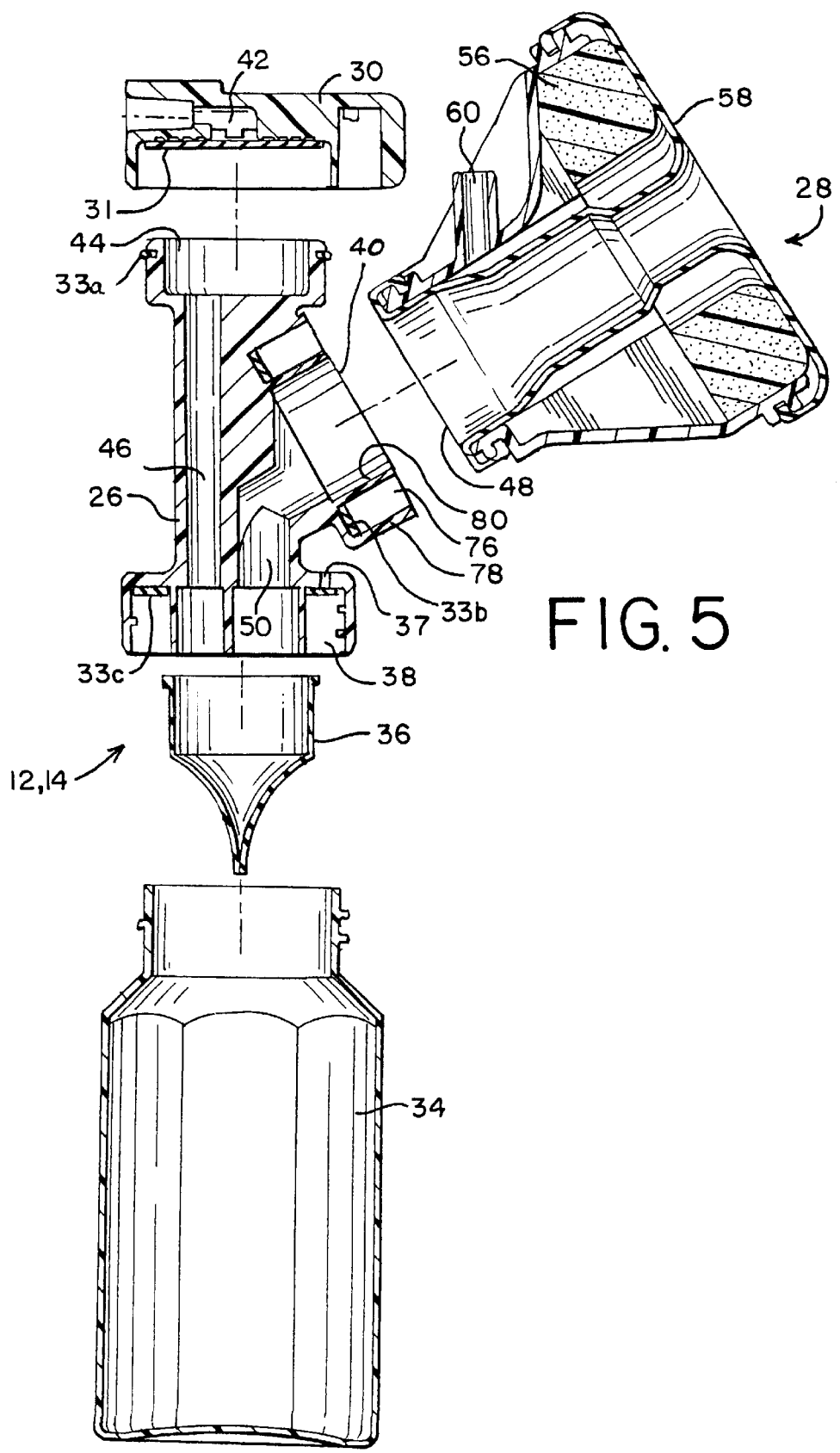
FIG. 5 is an exploded view of the collector of FIG. 2.

The expressers 12, 14 are shown in greater detail in FIGS. 2, 3 and 5. Each expresser includes a manifold 26, a cup assembly 28 which fits over a breast, a cap 30, a filter 31 (FIG. 5), a sealing device 33a such as a wipe washer, o-ring or the like, and a collection vessel 34. Gaskets 33b and 33c are also included, to better seal the vacuum system. A valve 36 can be included, though it is not necessary. The collection vessel can be a bottle made of plastic-like material or the like or a bag, and can be oriented at an obtuse angle with respect to the cup assembly, as shown.

The manifold 26 includes an opening 38 which is preferably threaded, so that a collection vessel such as a plastic milk bottle can be threadedly secured to the manifold 26, with the valve 36. The valve 36 is preferably a one-way check valve such as a duck bill valve or the like. When using the valve 36, the gasket 33c is not needed because the valve 36 seals the opening 38. A vent 37 in the manifold 26 is helpful because it keeps the collection vessel 34 at atmospheric pressure when the valve 36 is used. However, it is also possible to eliminate the valve 36, in which case there is also no need for the vent 37.

A vacuum is applied to the expresser through a port 42 in the cap 30, and is drawn through a vacuum path in the manifold 26 through an outlet opening 44 in the top of the manifold. The vacuum is drawn through an internal orifice 46 to the opening 38 in the midsection of the vacuum path, which is beneath the port 42 and the cup assembly 28. The vacuum tends to close the valve 36, which in conjunction with the vent 37, prevents a substantial buildup of vacuum in the collection vessel 34.

The vacuum is drawn from the opening 38 to a manifold vacuum inlet 40 through a channel 50. The vacuum inlet 40 forms a cup assembly opening that is in communication with a milk outlet port 48 in the cup assembly 28. When milk is drawn from the breast, the milk passes through the channel 50 under the force created by the vacuum, but most of the milk drops into the valve 36 through the force of gravity, and does not enter the orifice 46. Cleaning is easier because milk is not drawn into the vacuum path beyond the collection vessel 34. When sufficient milk collects in the valve 36, the weight of the milk forces the valve open, which releases the milk into the collection vessel 34. Because the milk falls down, the vacuum lines are not contaminated. In this manner, the milk is collected without contaminating the vacuum lines 18, 20 (FIG. 1).

The cup assembly 28 has a milk inlet port 52 in addition to the outlet port 48. The components of the cup assembly 28 include a bell housing 54, a donut shaped pad 56, and a flexible liner 58, shown disassembled in FIG. 4. The cup assembly 28 also has an air pressure pulsation port 60 which forms part of a pressure path and allows pressurized air to enter a space 62 between the case bell housing 54 and the liner 58.

The cup assembly 28 is assembled by placing the donut shaped pad 56 in the housing 54 as shown, and does not need further securement. The pad 56 is preferably made of a suitable foam material which is sized to fit snugly in the housing 54. However, the pad 56 can be easily removed by placing a finger through the opening in the ring and pulling the ring out.

Figure 4:
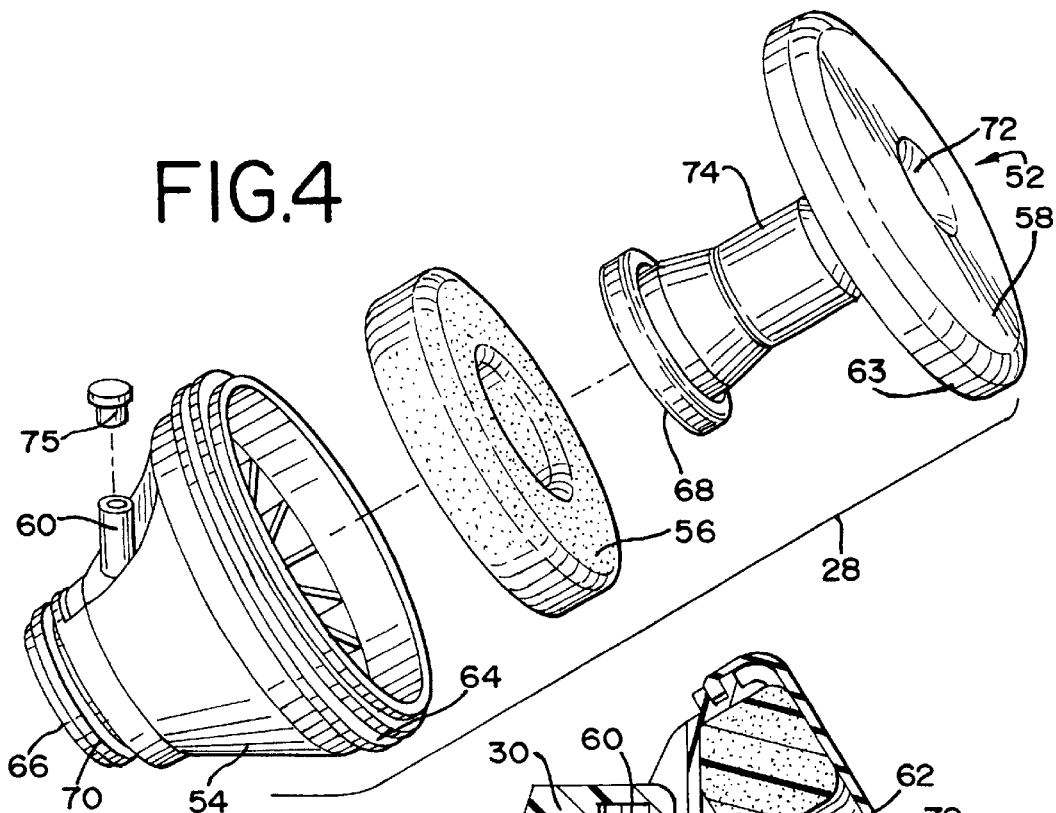
FIG. 4 is an exploded view of a cup assembly used in the collector of FIG. 2.

The liner 58 is installed in the cup assembly 28 by securing an end 63 to the liner 58 in a groove 64 formed in the housing 54 (FIGS. 2, 3 and 4). The end 63 and groove 64 are shaped to provide locking press fit type of securement. The liner could also be affixed to the housing 54 by heat or chemical bonding.

The liner 58 extends from the groove 64 over and around the pad 56 and inside of the housing 54 to a bottom end 66 of the housing 54. An end 68 of the liner 58 is inserted into a groove 70 near the end 68 for securement in a press fit fashion. The liner 58 can be any suitable shape, including the shape shown in FIG. 2, which includes a relatively narrow section 72 near the inlet opening 52, and a wider section 74 between the section 72 and the outlet end 48 of the cup assembly 28. This shape places more pressure around the areola region of the breast, while placing less pressure on the nipple itself. By sealing the liner to the case at both ends, the assembly can be washed without taking the liner off, if a cleaning cap 75 is placed over the pressure inlet 60 (FIG. 4).

Figure 6:
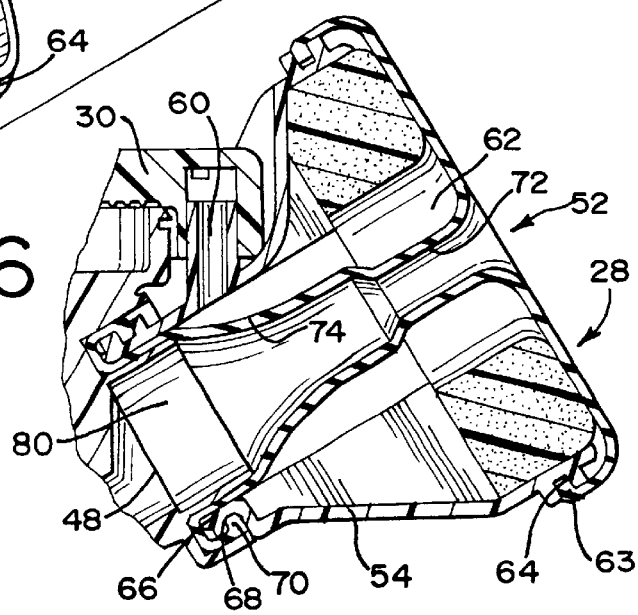
FIG. 6 is a cut-away view of the collector of FIG. 2, showing the liner in a collapsed condition.

The cup assembly 28 can be press fit into a circular groove 76 in the manifold 26, seen in FIG. 5. The groove 76 is formed by an outside wall 78 and an inside boss 80. The boss 80 can extend outwardly as far as desired, and can be any suitable shape, such as circular, triangular, square, rectangular, elliptical, hexagonal, etc. Since the boss 80 is hollow and prevents the liner 58 from collapsing under outside air pressure, the boss 80 protects any part of the nipple which is inside the boss from a pinching action caused by pressure when the liner is collapsed, as seen in FIG. 6. Abrasion is avoided because there is more room for breast extension during milk expression. The boss 80 also keeps the throat of the cup assembly open, so that the flow of milk is not inhibited.

The cap 30 (FIGS. 2, 3 and 5) includes an air pressure/pulsation channel 82 which extends from a pressure inlet 84 to the port 60, as well as the port 42 for the vacuum path. The cap 30 can be press fit over the manifold opening 44 and the cup assembly air pressure/pulsation port 60, and can be easily removed. When installed, the cap 30 farther secures the cup assembly in the manifold, but both the cap and the manifold can be removed without tools for cleaning purposes.

The filter 31, if used, further prevents liquids, fats and solid components in the milk from entering the vacuum lines and the pump. The filter 31 is preferably permeable to air flow when dry and also when wet, which can happen if milk contacts the filter. Thus, if the filter becomes wet due to milk and/or water, air can still pass through the filter because the filter remains permeable to air. An example of such a filter is Versapor R1200 (part no. 66393) by Pall Corp.

Referring again to FIG. 1, the pump 16 has two halves 104, 106 secured together by screws or the like 108 to form a chamber 110. The screws 108 also secure a movable diaphragm 112 in place. The diaphragm 112 divides the chamber 110 into two halves 110a, 110b.

The diaphragm 112 is oscillated in a back and forth manner by a motor 114. About 41–65 pulsations per minute at the breast (one pulsation being the result of both a back and forth motion of the diaphragm) are believed to produce suitable results, with about 52 pulsations per minute producing good results. The motor can be secured to the housing by bolts 116 or the like.

The motor 114 can be a stepper motor, which is one form of a linear actuator, which has a shaft 118. The shaft 118 moves in and out of the motor 114 in the axial direction without rotation. The shaft 118 is threaded, and is moved by a rotating threaded ring 120, which is similar to a nut. Rotation of the ring 120 moves the shaft 118 linearly. In this manner, the shaft 118 can move the diaphragm 112 back and forth essentially directly, without large, complex linkages.

The distal end of the shaft 118 can be guided by an opening 122 in an end cap 124. The end cap 124 is secured by bolts 126.

The pump 16 also has vacuum outlets 128, 130 in the chamber 110, on opposite sides of the diaphragm 112. The vacuum lines 18, 20 are connected to the vacuum outlets 128, 130. Check valves such as duck bill valves 136, 138 control the vacuum and pumping operation, and exhaust valves 140, 142 release the pressure created in the chamber halves 110a, 110b by the movement of the diaphragm 112. However, some of the pressure generated by the diaphragm is transmitted through the pressure lines 22, 24 to the collectors 12, 14. The pressure forces the liners 58 against the breasts (see FIG. 6), which further stimulates release of milk. While the vacuum is fairly continuous, though, the pressure pulsates, in part because the pressure is quickly bled through vents 143 in the pressure lines 22, 24. In fact, when the diaphragm moves away from a pressure line 22, or 24, air is drawn out and a partial vacuum can be created.

Figure 7:
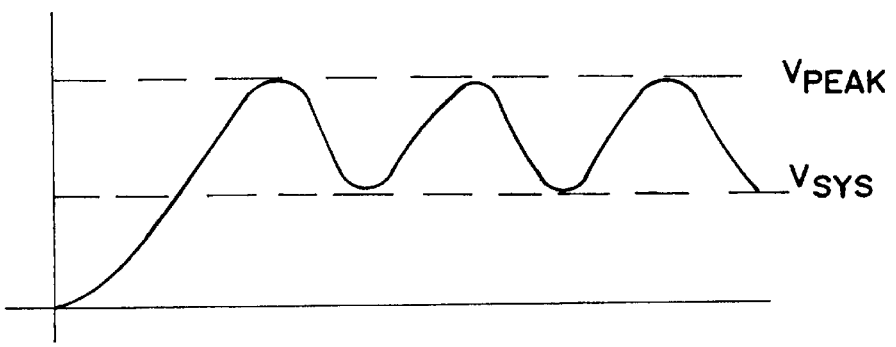
FIG. 7 is a graph showing the effect of pressure pulsation on the vacuum at the liner of the collector of FIG. 2.

FIG. 7 shows the effect of adequately vented pulsation pressure on the vacuum supplied to the liner. The pump 16 generates a vacuum $V_{SYS}$. Without pulsation pressure, the vacuum is fairly steady at $V_{SYS}$. When pressure pulses are applied to the outside of the liner, though, the vacuum periodically increases to $V_{PEAK}$. Those periodic increases stimulate milk production with less discomfort and a lower $V_{SYS}$ than is needed if pressure pulses are not applied.

Preferably, a minimum $V_{SYS}$ of 0.5" mercury is maintained during use, and the maximum vacuum $V_{PEAK}$ does not exceed 5" mercury. The maximum vacuum $V_{PEAK}$ is preferably 3.0"–4.1" mercury. However, the maximum differential between $V_{SYS}$ and $V_{PEAK}$ is preferably between 1" and 4.5" mercury. The vents 143 are sized to obtain a desired $V_{PEAK}$, and avoid stalling due to overload. If the vents are too small, $V_{PEAK}$ will be too high and stalling could occur. If the vents are too large, $V_{PEAK}$ will be too low.

Figure 8:
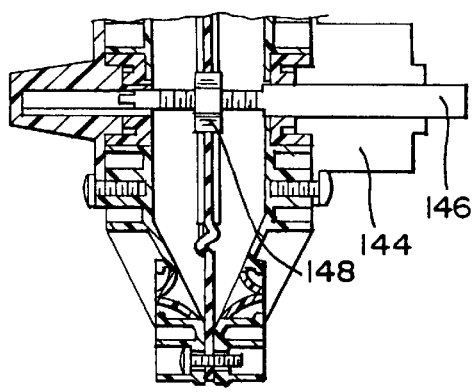
FIG. 8 is a cut-away view of an alternate embodiment of the pump used in the apparatus of FIG. 1.

The device is light weight, portable and compact because large motor linkages are eliminated. Wear is also reduced by simplifying the power train in this manner. The motor 114 can be any suitable device which creates a fairly self-contained drive system which is relatively small in size and fairly quiet. In fact, the motor can be an ordinary motor 144 with a threaded rotating shaft 146, as seen in FIG. 8. In that embodiment, a fixed ring 148 is attached to the diaphragm. The ring 148 is also threaded, so when the shaft 146 rotates clockwise and counter-clockwise, the diaphragm 112 moves back and forth.

Figure 9:
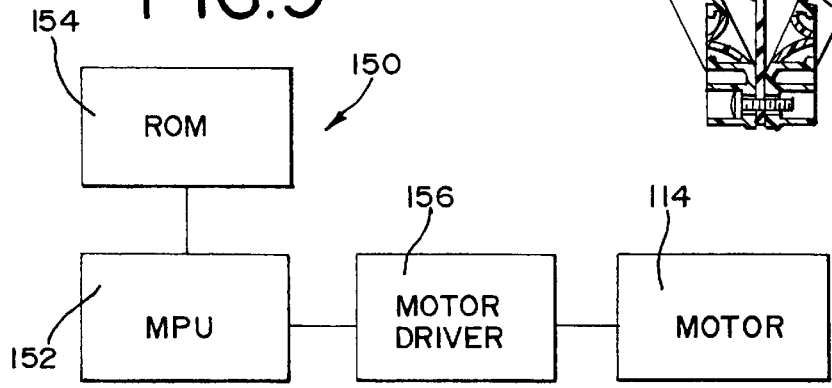
FIG. 9 is a block diagram of a control system for the apparatus of FIG. 1.

The motor can be controlled in any suitable manner, such as the control system 150 shown in FIG. 9. An application specific integrated circuit or the like has an MPU (Micro Processing Unit) 152 and a ROM (Read Only Memory) 154, programmed to cause a motor driver 156 to set the desired rate of rotation and the direction of rotation of the motor. The rotation rate, as well as the timing of the back and forth motion of the diaphragm, can be controlled in this manner.

Figure 10:
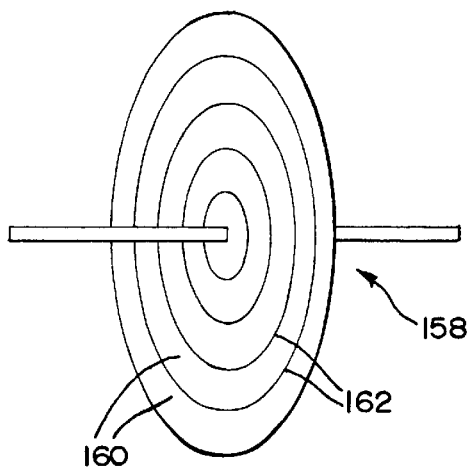
FIGS. 10 and 11 are diagrams of an alternate embodiment of the diaphragm used in the pump in the apparatus of FIG. 1.
Figure 11:
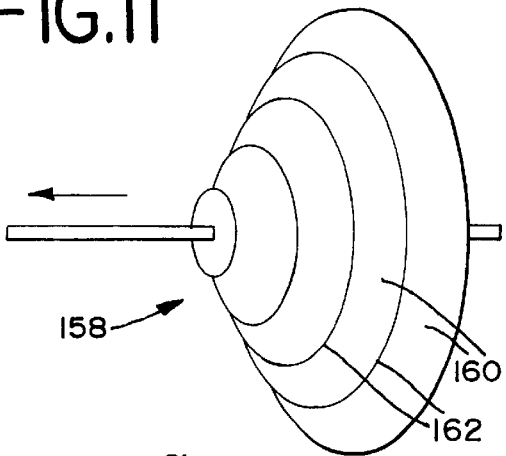

The diaphragm 112 can be any suitable configuration, such as that shown in FIG. 1, which features a flat stiff middle section flanked by soft corrugations. Another design is shown in FIGS. 10 and 11, where a diaphragm 158 has a plurality of rings 160 joined by corrugations 162.

In use, power is applied to the pump 16, and the expressers 12, 14 are placed over the breasts. The vacuum $V_{SYS}$ created by the pump 16 secures the expressers 12, 14 on the breasts and helps draw milk from the breasts. The pressure pulsations massage and compress the breasts to stimulate milk production, and reduce the amount of vacuum needed to collect the milk. The air pressure lines are vented to obtain strong pulses without overloading the system. This reduces discomfort to the breasts. The device can be easily disassembled without tools, cleaned and reassembled.

The many advantages of this invention are now apparent. The pulsation pulses stimulate milk production, without overloading the system due to excessive pressure build-up in the pressure lines. Cleaning is more convenient because milk does not enter the vacuum lines. Moreover, the entire collector can be easily disassembled for cleaning and reassembled without tools. The bosses in the expressers protect the end of the nipple from irritation, which is comfortable. Moreover, the entire pump is small, lightweight and relatively quiet.

While the principles of the invention have been described above in connection with a specific apparatus and applications, it is to be understood that this description is made only by way of example and not as a limitation on the scope of the invention. For example, various aspects of the invention could be used to milk animals, as well as humans.

What is claimed is:

1. Apparatus for expressing milk from a breast comprising
    a milk collector unit having
    a manifold, the manifold having a vacuum path, the vacuum path having an inlet, an outlet and a midsection between said inlet and said outlet, said outlet being connected to a vacuum source,
    a collection vessel operatively connected to said midsection of said vacuum path, and
    a cup assembly, said cup assembly having a housing with an inlet for the breast, and an outlet operatively connected to said inlet of said vacuum path in said manifold, said cup assembly also having a liner of substantially uniform thickness in said housing, the vacuum path passing within said liner, said liner being secured with respect to said housing to form a space with said housing which is in communication with a pulsating pressure path and a pulsating pressure source,
    a vent in said pulsating pressure path providing controlled relief of pressure during the positive and negative portions of the pulsation cycle, and
    means for increasing the area for breast extension during milk expression.

2. The apparatus of claim 1 wherein said cup assembly includes a pad located in the input end of said housing.

3. The apparatus of claim 1 wherein the pressure in the pulsating path pulsates at a rate of 41 to about 65 pulses per minute.

4. The apparatus of claim 1 wherein the vacuum in the vacuum path varies between about 0.5" mercury and about 5" mercury through the pulsation cycle.

5. The apparatus of claim 1 comprising a filter between the vacuum source and the said outlet, said filter being substantially permeable to air when dry or wet, and substantially impermeable to liquid, fats and solid components in the milk.

6. The apparatus of claim 1 wherein said milk collector unit further includes a removable cap, said cup assembly being secured to said milk collector unit by both said manifold and said cap.

7. The apparatus of claim 6 wherein said vacuum path passes through said cap and said manifold to said cup assembly, and
    said pulsating pressure path passes through said cap to a pressure port in said cup assembly, said pressure port being in communication with said space between said housing and said liner.

8. The apparatus of claim 1 wherein said vacuum source and said pulsating pressure source comprise an air pump having a movable diaphragm in a chamber, a shaft which passes through said diaphragm and a motor which moves said diaphragm axially, said motor rotating around the axis of said shaft.

9. Apparatus for expressing milk from a breast comprising
    a milk collector unit having
    a manifold, the manifold having a vacuum path, the vacuum path having an inlet, an outlet and a midsection between said inlet and said outlet, said outlet being connected to a vacuum source,
    a collection vessel operatively connected to said midsection of said vacuum path,
    a cup assembly, said cup assembly having a housing with an inlet for the breast, and an outlet operatively connected to said inlet of said vacuum path in said manifold, said cup assembly also having a liner of substantially uniform thickness in said housing, the vacuum path passing within said liner, said liner being secured with respect to said housing to form a space with said housing which is in communication with a pulsating pressure path and a pulsating pressure source, and
    means for increasing the area for breast extension during milk expression,
    wherein the pressure in the pulsating path pulsates at a rate of 41 to about 65 pulses per minute.

* * * * *